United States Patent
Caldow et al.

(10) Patent No.: US 9,035,242 B2
(45) Date of Patent: May 19, 2015

(54) INSTRUMENT FOR SIZING NANOPARTICLES AND A COMPONENT THEREFOR

(71) Applicant: TSI, INCORPORATED, St. Paul, MN (US)

(72) Inventors: Robert Caldow, Roseville, MN (US); Jason Johnson, St. Paul, MN (US)

(73) Assignee: TSI INCORPORATED, St. Paul, MN (US)

( * ) Notice: Subject to any disclaimer, the term of this patent is extended or adjusted under 35 U.S.C. 154(b) by 0 days.

(21) Appl. No.: 14/372,279

(22) PCT Filed: Jan. 18, 2013

(86) PCT No.: PCT/US2013/022224
§ 371 (c)(1),
(2) Date: Jul. 15, 2014

(87) PCT Pub. No.: WO2013/109942
PCT Pub. Date: Jul. 25, 2013

(65) Prior Publication Data
US 2014/0339415 A1 Nov. 20, 2014

Related U.S. Application Data

(60) Provisional application No. 61/589,098, filed on Jan. 20, 2012.

(51) Int. Cl.
*H01J 49/24* (2006.01)
*G01N 27/62* (2006.01)
*G01N 15/10* (2006.01)
*H01J 49/22* (2006.01)
*G01N 15/06* (2006.01)
*G01N 15/00* (2006.01)
*G01N 15/02* (2006.01)
*G01N 1/22* (2006.01)

(52) U.S. Cl.
CPC ............ *G01N 27/624* (2013.01); *G01N 15/065* (2013.01); *G01N 2015/0046* (2013.01); *G01N 15/0255* (2013.01); *G01N 2015/0038* (2013.01); *G01N 1/22* (2013.01); *G01N 15/10* (2013.01); *G01N 2015/1087* (2013.01); *H01J 49/22* (2013.01)

(58) Field of Classification Search
USPC .......................................... 250/286, 288, 281
See application file for complete search history.

(56) References Cited

U.S. PATENT DOCUMENTS

| | | | |
|---|---|---|---|
| 5,072,626 A | 12/1991 | Ensor et al. | |
| 5,922,976 A | 7/1999 | Russell et al. | |
| 2005/0162173 A1* | 7/2005 | Mirme | 324/458 |
| 2005/0173629 A1 | 8/2005 | Miller et al. | |
| 2006/0284077 A1 | 12/2006 | Fissan et al. | |
| 2008/0264491 A1 | 10/2008 | Klee et al. | |
| 2010/0001184 A1* | 1/2010 | Chen et al. | 250/307 |

* cited by examiner

*Primary Examiner* — Kiet T Nguyen
(74) *Attorney, Agent, or Firm* — Kagan Binder, PLLC

(57) ABSTRACT

An improved nanoparticle sizing apparatus comprised of a unipolar charger operatively coupled to a radial differential mobility analyzer in combination with a condensation particle counter and powered by a power source such as a battery or solar cell, thereby providing a portable sizing device.

17 Claims, 17 Drawing Sheets

INSTRUMENT FOR SIZING NANOPARTICLES AND A COMPONENT THEREFOR

CLAIM OF PRIORITY TO PRIOR APPLICATION

The present application claims priority to International Application No. PCT/US2013/022224, filed on Jan. 18, 2013, which in turn claims priority to and the benefit of U.S. Provisional Application No. 61/589,098, filed Jan. 20, 2012, the disclosures of which are hereby incorporated by reference in their entireties.

BACKGROUND OF THE INVENTION

The invention relates to systems and devices for measuring concentrations of nanometer or ultrafine particles, and more particularly to such systems that are adjustable in terms of their sensitivities to certain sizes or electrical mobilities of particles or sets of particles that fall within the nanometer size range.

When materials are produced or formed in the nanometer size range, i.e. from about 1 micrometer in diameter down to molecular levels, they exhibit unique properties that influence their physical, chemical and biological behavior. Nanotechnology, the field of endeavor concerned with materials in this size range, has experienced explosive growth over the last several years as new and diverse uses for nanomaterials are discovered and developed throughout a broad range of industries.

These developments have raised concerns, because the occupational health risks associated with manufacturing and using nanomaterials are not clearly understood. Many nanomaterials are formed from nanoparticles initially produced as aerosols or colloidal suspensions. Workers may be exposed to these particles through inhalation, dermal contact and ingestion, at increased levels due to working environments with nanoparticles in concentrations that far exceed ambient levels.

Traditionally, health related concerns about airborne particles have focused on particle concentrations in terms of mass per unit volume. Under this approach, permitted maximum concentration standards are determined, and mass concentrations are measured with respect to these standards. However, toxicologic studies involving ultrafine particles (0.1 micron diameter and below) suggest that particle surface area, as compared to particle mass, is the better indicator of health effects. This may follow from the fact that for any given shape (e.g. spherical), the smaller the particle, the greater is its surface area compared to its volume or mass. A proportionally larger specific surface area (i.e. surface area divided by mass) increases the tendency of a particle to react with chemicals in the body. Moreover, due to the small mass of nanoparticles, mass concentration measurements are difficult to obtain and lack the requisite sensitivity, even when based on particle accumulation such as through collection of particles on a filter. Additional studies have also suggested that health effects may also be correlated with the number of inhaled ultrafine particles that impact the lungs. Accordingly, instruments that measure particle concentrations in terms of surface area and particle number in the nanometer size range are expected to provide more useful assessments of health risks due to nanoparticle exposure.

SUMMARY OF THE INVENTION

In one example embodiment of the invention, a nanoparticle scanning and sizing system is disclosed that is compact, portable and capable of size distributions down to 10 nanometers and able to measure in both SCAN mode for real-time size distributions and in SINGLE mode for single electrical mobility concentration monitoring. One minute size distributions along with one second single size data can also be obtained from the novel and compact aerosol system. (a sizing device with a wide size and concentration range).

In a related embodiment, an improved nanoparticle sizer instrument is described herein that facilitates portability and operation with other optical sizers to increase particle size measurement range. In one example embodiment, three orders of size magnitude, such as from about 10 nanometers to about 10 microns, is measurable and facilitates real-time data collection. In related embodiments, the sizing system described herein will size particles down to the 2.3 nm and 1 nm size. Sizing below these levels may necessitate alterations in some hardware components. In addition, portability is improved with the use of long life (about 8 hours), hot swappable batteries or alternatively, fuel cells. The general concepts described herein are applicable to other aerosol instruments and are not just limited to nanoparticle sizing.

In yet another related embodiment, an RDMA (radial differential mobility analyzer) is combined with a CPC (condensation particle counter) and a power source, such as a battery or solar cell, to create a portable SMPS (scanning mobility particle sizer). In yet another embodiment, an RDMA and an electrometer is configured for another sizing system.

In one example embodiment of the invention, a filtration manifold for use in connection with a nanoparticle sizer is described that improves serviceability, air flow and filtration as well as facilitating a compact and portable design. In addition, the overall manifold construct and modular arrangement of the manifold can be used in other aerosol instruments. In this example embodiment, the manifold design is an integrated, multi-unit system that includes pressure/flow controls, a series of coaxial pressure taps and a series of interconnected filters. The manifold assembly is also a modular system that is ideal to route airflow or stream inlets and outlets wherever convenient to effectuate the desired interconnections. In related embodiments, the manifold assembly is configured for use in most particle instruments and in most miniature devices that require serviceable filtered air handling/routing such as gas instruments, small scale nanoparticle manufacturing, and semiconductor and pharmaceutical manufacturing applications.

DESCRIPTION OF THE PREFERRED EMBODIMENTS

Following below are more detailed descriptions of various related concepts related to, and embodiments of, methods and apparatus for an improved system and method for sizing particles in the nanometer range for various applications. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Figure 1A:
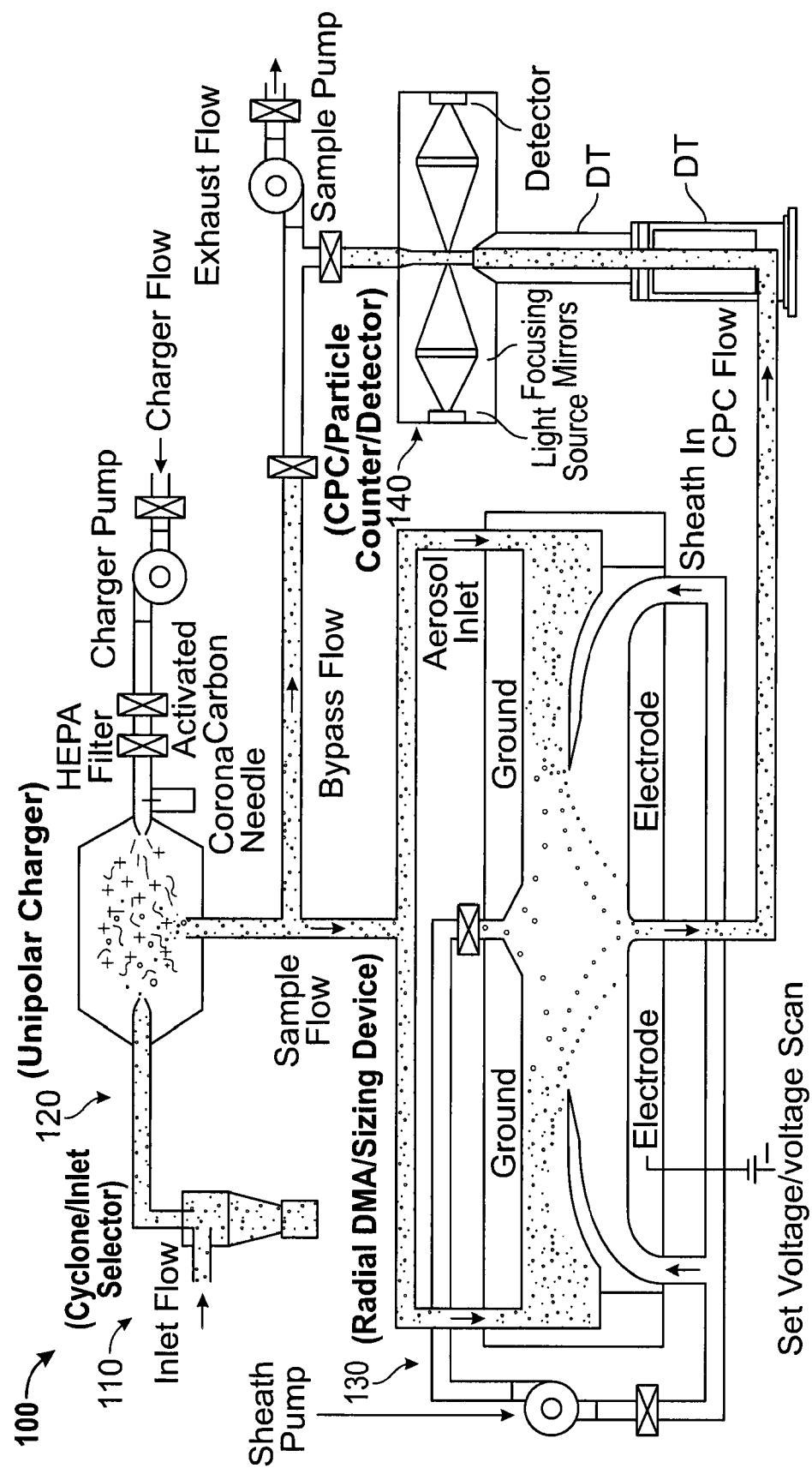
FIGS. 1A-1B are high level schematics of the nanoparticle sizing systems according to the invention.
Figure 1B:
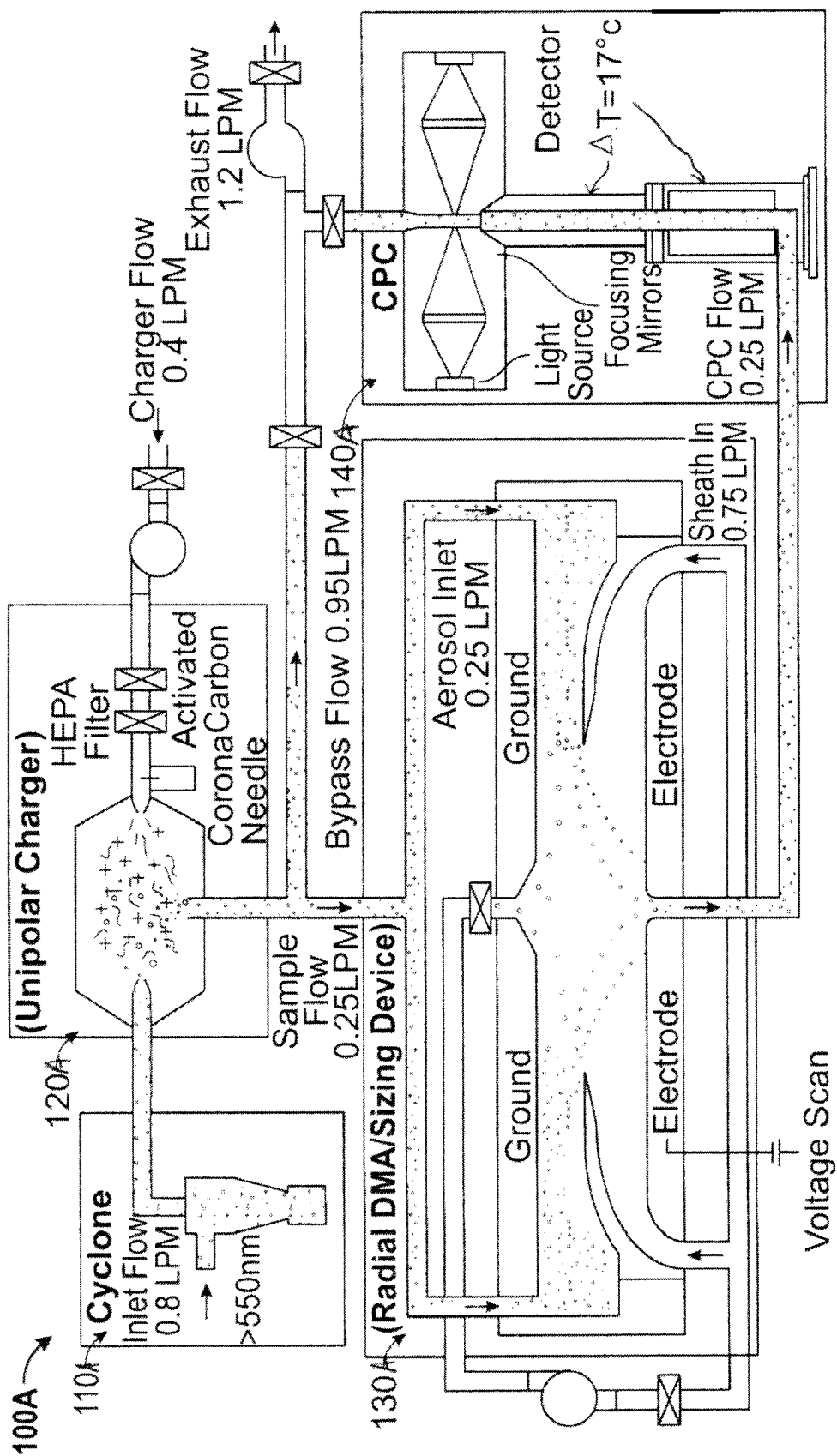

Referring now to FIGS. 1A-1B, there is shown an example embodiment of high level schematics of the nanoparticle sizing systems as well as a detailed example of a nanoparticle sizing system according to the invention. For purposes of simplicity, like numerals for like components will be used throughout the various figures disclosed herein with variations being designated as "a" or "b". A related system for measuring nanoparticles is also described in U.S. Pat. No. 7,812,306 issued on Oct. 12, 2010, entitled "Instruments for Measuring Nanoparticle Exposure", which is herein incorporated by reference in its entirety.

FIG. 1A discloses a nanoparticle sizing system 100 that includes a cyclone assembly 110 that is adapted for air sample inlet and for initial particle separation (such as removing larger particles in a pre-conditioning stage) which is coupled to a unipolar charger assembly 120 adapted to charge particles before being directed to a size selection stage of the system. The ion corona charger that forms part of the various embodiments of the nanoparticle sizing system described herein is described in U.S. Pat. No. 6,544,484, issued on Apr. 8, 2003, entitled "Aerosol Charge Adjusting Apparatus Employing a Corona Discharge", which is herein incorporated by reference in its entirety. In related embodiments, system 100 will size and count particles or measure particle concentration (generating a particle size distribution in various formats and dimensional weightings) over a wide size range (of about 1-1000 nm, and preferably 10-600 nm in the prototype) and a wide variety of concentrations (about 0- to about $1 \times 10^8$ particles/cm$^3$, and preferably 0- to $1 \times 10^6$ particles/cm$^3$ in another embodiment of the device).

Assembly 120 is then coupled to the size selection stage which in this example embodiment is a differential mobility analyzer (DMA) device 130, such as, but not limited to, a radial DMA, used for size resolution and accuracy of the particles to be measured. The radial DMA (RDMA) unit in this example embodiment contributes to system 100's compactness and light weight. The particles exiting DMA 130 are then directed to a condensation particle counter (CPC)140. In this example embodiment, CPC 140 is an isopropyl-based CPC adapted to provide accurate measurements at high and low concentrations using a working fluid to facilitate condensation (other working fluids include but is not limited to butanol, isopropanol, other alcohols, hydrocarbons, etc.). A suitable working fluid may be chosen, such that toxicity and special handling requirements are minimized. In a related embodiment, system 100 is configurable to use a water-based CPC where toxicity is of concern (see U.S. Pat. No. 6,712,881 to Hering et al, which is incorporated herein by reference in its entirety). In this example embodiment, the instrument is operable off a rechargeable wick with an eight hour life or longer if an external liquid reservoir and power source are used. FIG. 1B illustrates a similar embodiment as in system 100 but provides a nanoparticle sizing system 100A that provides more specifics as to the various air flow speeds and particle sizes.

In various related example embodiments, an optional inlet selector for eliminating particles of particular size and/or properties from the sample to be measured. The optional inlet selector includes but is not limited to a cyclone, an impactor, or a virtual impactor. The inlet selector serves to prevent interference from large particles (those outside the instrument measurement range) in less controlled aerosols. In yet another related embodiment, this component may be excluded from the device when measuring a well-controlled aerosol of a limited size range. Additionally, as the pressure drop across an inlet selector typically varies predictably as a function of inlet flow rate, it can be used as a portion of the system that measures the inlet flow rate in the device (which is useful for measuring absolute concentration of particles).

Referring again to unipolar charger 120 of FIGS. 1A-1B, the unipolar charger is used to apply a net charge (either positive or aerosol) to an aerosol. In various embodiments, the unipolar charger is either of a diffusion-type or Corona-type for charging aerosol so that the particle can be classified by their electrical mobility diameter. As compared to a bipolar charger (or neutralizer), the charging efficiency of a unipolar charger is much greater, especially at smaller sizes (<30 nm), thereby improving counting statistics when measuring size distributions of very small aerosol particles. The unipolar charger described herein is powered electrically, with relatively low power consumption, is compact in size, is consistent in its charging ability, is effective when used with small flows of clean and particle-laden gases, as are required by this type of device and does not use radioactive or other regulated materials. In various related example embodiments, the electrical charging device is selected from the group consisting of a unipolar charger, a corona tip and metal mesh or screen arrangement, a diffusion charger, a photoionization charger, an ultraviolet light charger and an X-ray aerosol charger.

Referring again to RDMA 130 of FIGS. 1A-1B, the RDMA operates in system 100A as an electrically powered band-pass particle filter that transmits a narrow range of charged particles of a given electrical mobility diameter (which is a function of the particle's size and of how much charge it has acquired from the aforementioned unipolar charger). Typically, the voltage on the RDMA (which controls the electrical mobility diameter that passes through the RDMA) is varied, either by scanning continuously or by stepping in a pre-defined pattern, or is fixed voltage if a measurement of the concentration of particles of a single electrical mobility diameter is required. Hence, measuring the concentration of the particles that pass through the RDMA yields measurements are usually convertible to a particle size distribution. Finally, the compact size and weight of the RDMA aids in size reduction of system 100 while still providing a comparably wide size range, especially for the low flows required of a small portable device. The RDMA's compact size also makes it compatible with the compact pumps and controls that can be used with such a low power consumption, portable device. Reference is made to U.S. Pat. No. 5,117,190 to Michel Pourprix for a further description on the operation of an RDMA, the disclosure of which is hereby incorporated by reference in its entirety. In various related embodiments, the differential mobility analyzer is selected from the group consisting of a radial differential mobility analyzer, a cylindrical differential mobility analyzer, parallel plate differential mobility analyzer and a precipitator of various geometries.

Referring again to CPC 140 of FIGS. 1A-1B, once exiting the RDMA, the number of particles present in, or the concentration of particles in, the size-classified aerosol is measured by CPC 140 detector. The CPC yields the highest accuracy and sensitivity of any method for measuring particle number, as it is capable of detecting individual particles, regardless of their charge state (as an electrometer might require). Robust, low-power, small size variants of CPC can be used, as are used in this device, thereby enhancing portability. In a related embodiment, to enhance portability as well as long-term usage, an optional system for delivering the CPC working fluid is included along with the removable wick that can be externally loaded with working fluid. This option supplements working fluid reservoir system provided in system 100.

Figure 2A:
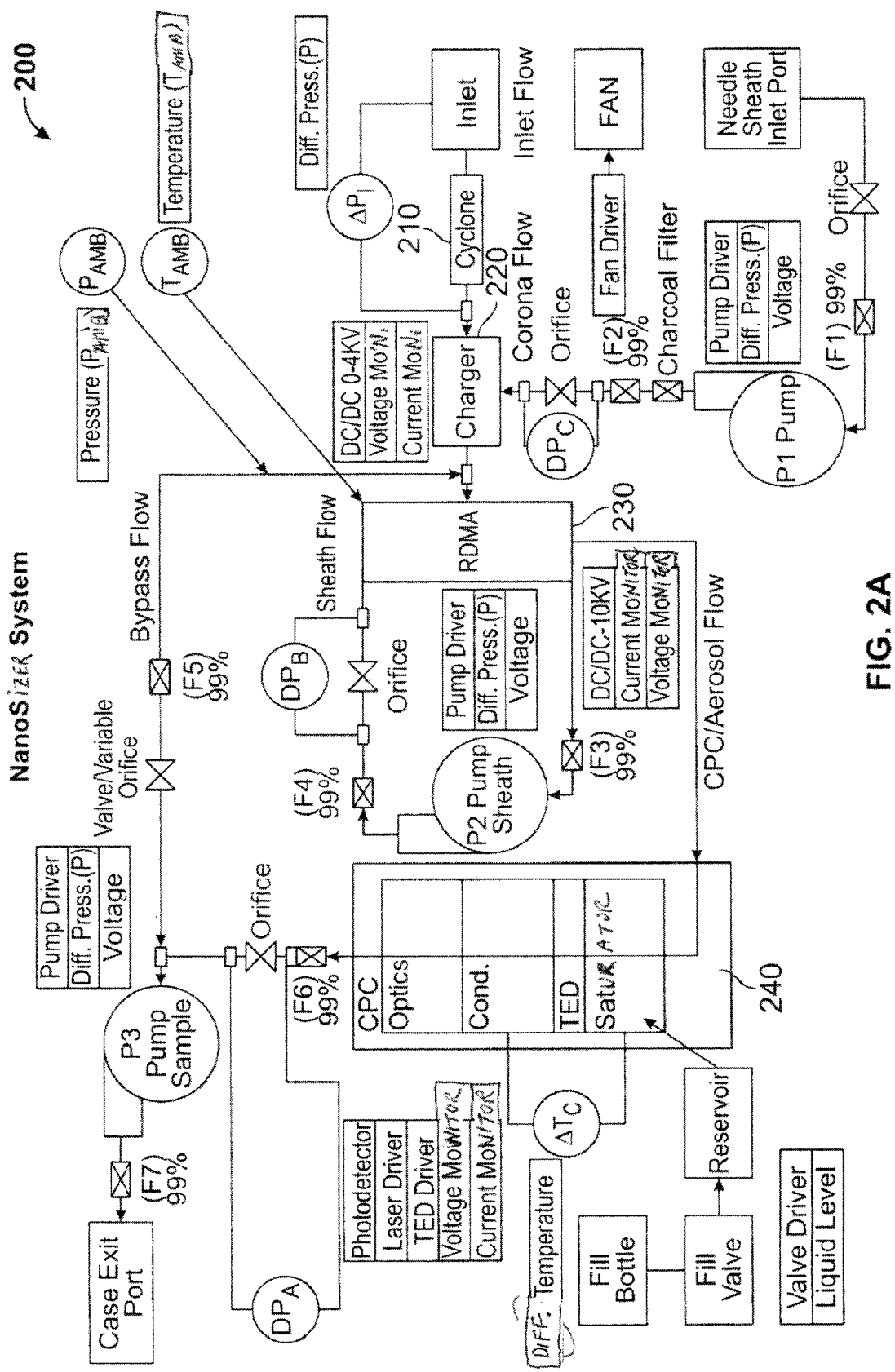
FIGS. 2A-2B are detailed schematics of the nanoparticle sizing systems according to the invention.
Figure 2B:
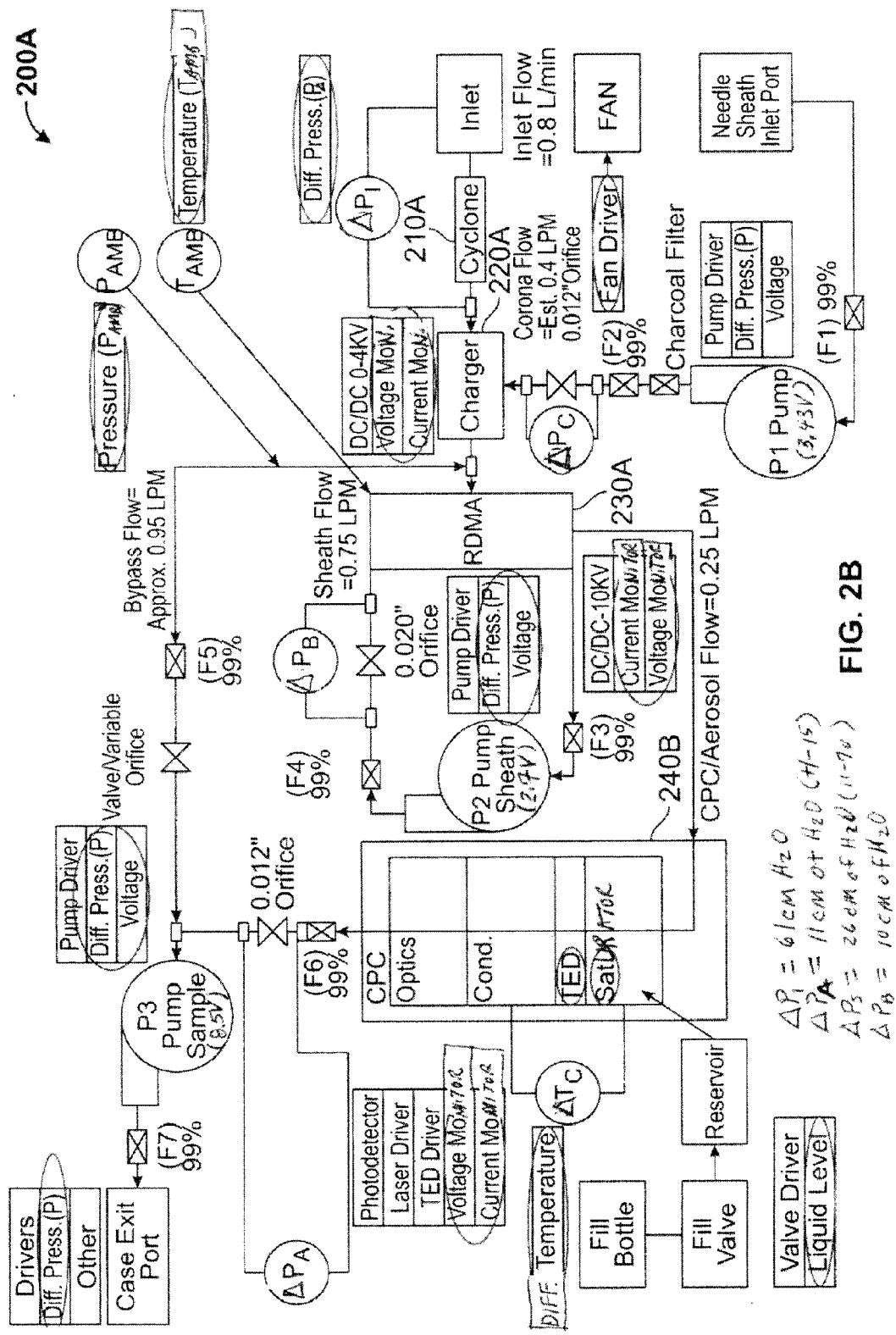
Figure 3:
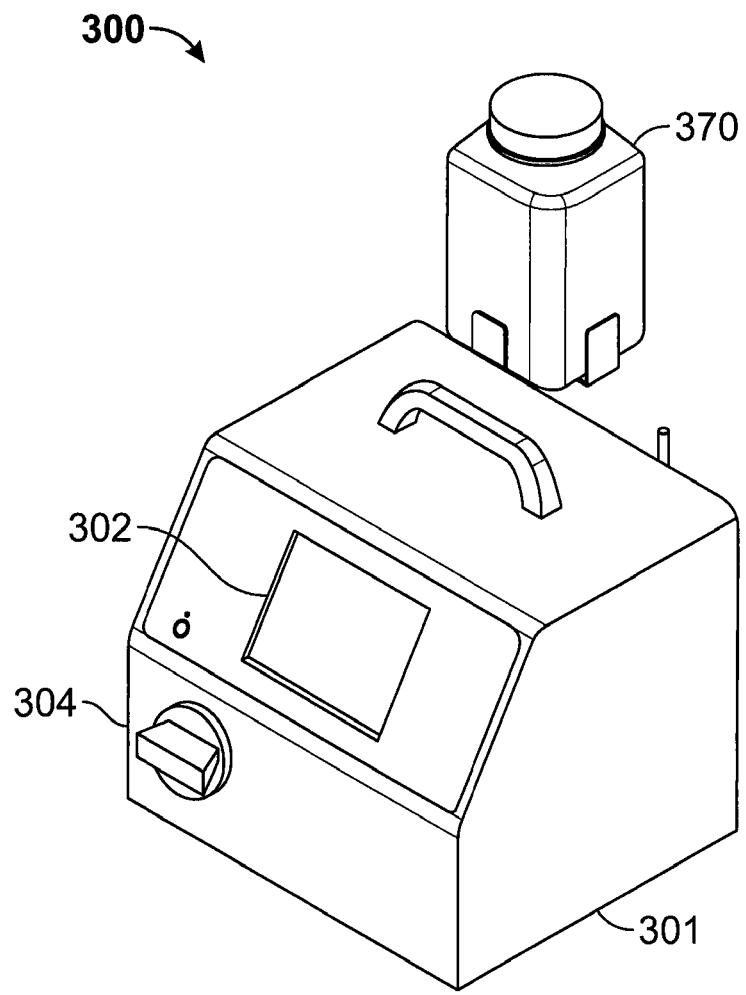
FIG. 3 is a perspective view of a portable nanoparticle sizing system according to the invention.

Similar to systems 100 and 100A, FIGS. 2A-2B illustrate more detailed schematics of the nanoparticle sizing systems 200 and 200A according to the invention. These systems also include a fill bottle, a control valve for metering the working fluid from the fill bottle, a reservoir for putting the working fluid in contact with the CPC wick, and various tubes, seals, connectors and the like for enabling this function.

Referring now more specifically to example embodiments of nanoparticle sizing systems 200 and 200A, an aerosol is received at an inlet conduit 202A (with an inlet flow rate of about 0.75 lpm) and directed through a large-particle separator such as a cyclone 210A, to remove particles having aerodifferential diameters that exceed one micron. The flow of particles then flow from cyclone 210A into unipolar corona charger 220A. At corona needle sheath inlet 204A, air is pumped by a pump 205A through a charcoal filter 206A and a high efficiency particle air (HEPA) filter 207A, thereby providing a corona flow of about 0.4 lpm of ion charged air into charger 220A via a corona needle 208A (not shown but within charger 220A and which is biased to a high positive voltage e.g. 4 kilovolts and generates positive ions at its tip); which mixes with air from cyclone 210A within the charger body exiting through an orifice 209A. Meanwhile, the remaining flow from cyclone 210A is conducted into charger body or chamber 220A through another orifice, for a turbulent mixture with the positive ions to effect a diffusion charging of the particles suspended in the aerosol. A portion of positively charge air flow is channeled into a bypass tube 221A at a flow rate of about 0.9 lpm, through a filter 222A and through a valve and orifice assembly 223A with a pump 224A. The filtered air passes through another filter 225A before exiting through port 226A.

The aerosol leaving mixing chamber 220A includes a suspension of positively charged particles and positive ions that is then channeled into a radial differential mobility analyzer (RDMA) 230A with the help of a sheath flow of clean air. The sheath flow is formed from part of the particle laden air flowing into tube 232A which is filtered through a filter 233A and is drawn by a pump 234A. The pumped air flows through a filter 236A and through an orifice 237A (about 0.020 inch in size) and eventually is redirected into RDMA 230A as the clean air sheath flow at a flow rate of about 0.75 lpm. In related embodiments, the sheath flow rate is as high as 4 lpm and charger flow rate as high as 2.5 lpm; with either flow rate being as low as 0.05 lpm as well.

Particle laden air of a predefined size particle size exits RDMA 230A as CPC/aerosol flow via a tube 239A at a flow rate of about 0.25 lpm and is fed into a CPC 240A. CPC 240A uses condensation particle counting technology as described in U.S. Pat. No. 4,790,650 to Keady and U.S. Pat. No. 5,118,959 to Caldow et al and an optical detection system as described in U.S. Pat. No. 6,831,279 to Ho et al, all of which are incorporated by reference in their entireties. Coupled to CPC 240A is a reservoir/fill valve assembly 250A adapted to continuously saturate a removable wick within CPC 240A. Assembly includes a fill bottle adapted for a user selected working fluid to be used by system 200A in CPC 230A. Once the particle laden air sample exits CPC 240A (after being counted and analyzed) it passes through a filter 242A and through an orifice 244A (about 0.012 inch in size) and exits into bypass tube 221A after which it exits the system through exit port 226A.

Although not specifically shown in the figures of systems 100, 100A, 200 and 200A, a novel pump and manifold assembly (as shown and discussed in more detail in FIGS. 7-9) is provided that facilitates the various connections between the various sample, sheath and charger pumps (other various other aerosol conduits) thereby enabling a more compact design of the nanoparticle sizing system described in more detail below.

Referring now to FIGS. 3-6, there are illustrated several views of portable nanoparticle sizing systems 100, 200 and 300 according to the invention. In this example embodiment, system 300 is encased in a housing 301 having a display screen 302 thereon (LCD or other flat display), a control button 304 and an optional fill bottle 370 for additional working fluid for the system.

Figure 4:
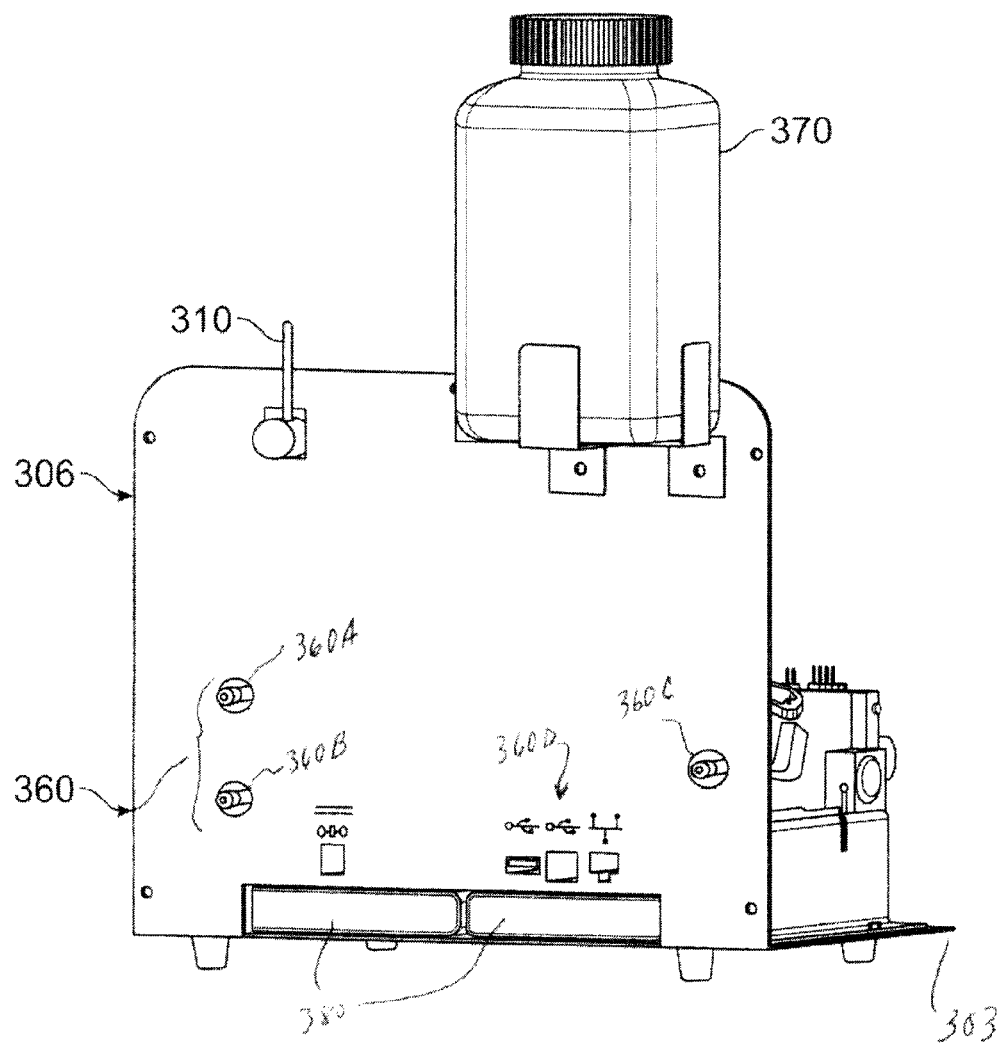
FIG. 4 is a rear view of the particle sizing system according to the invention.
Figure 5:
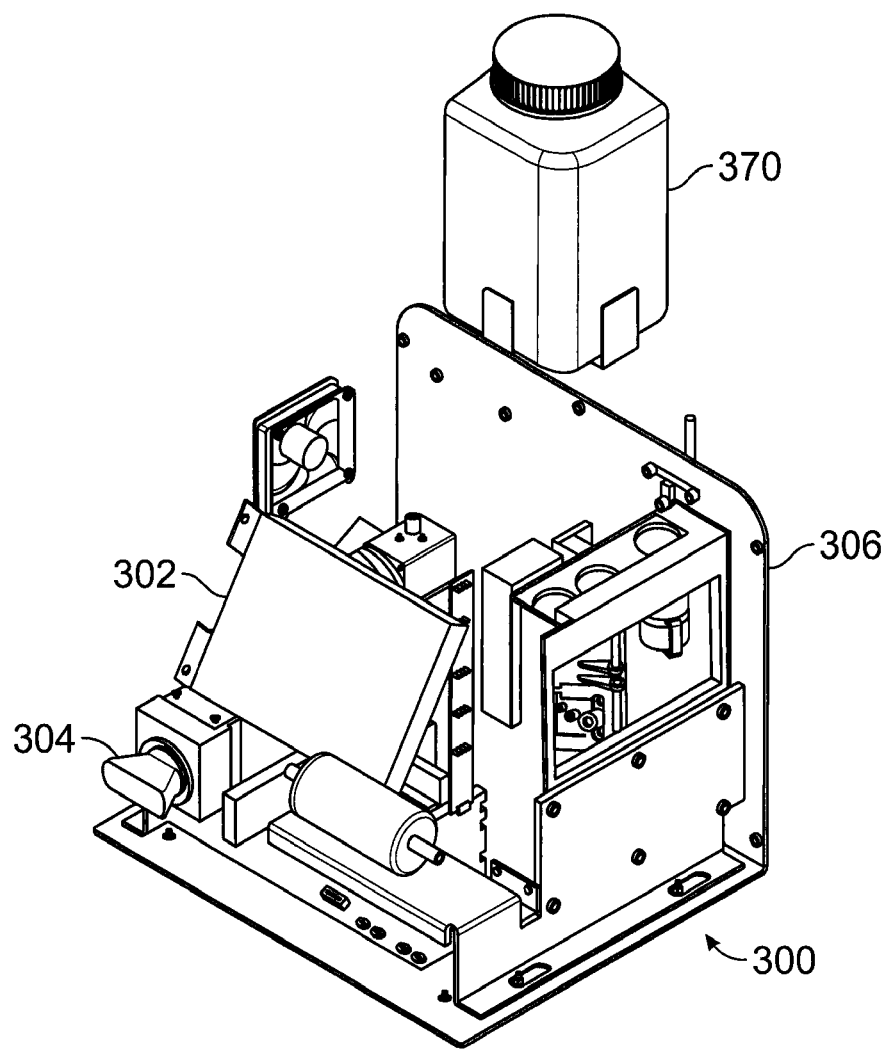
FIG. 5 is a partially exposed view of the particle sizing system according to the invention.
Figure 6:
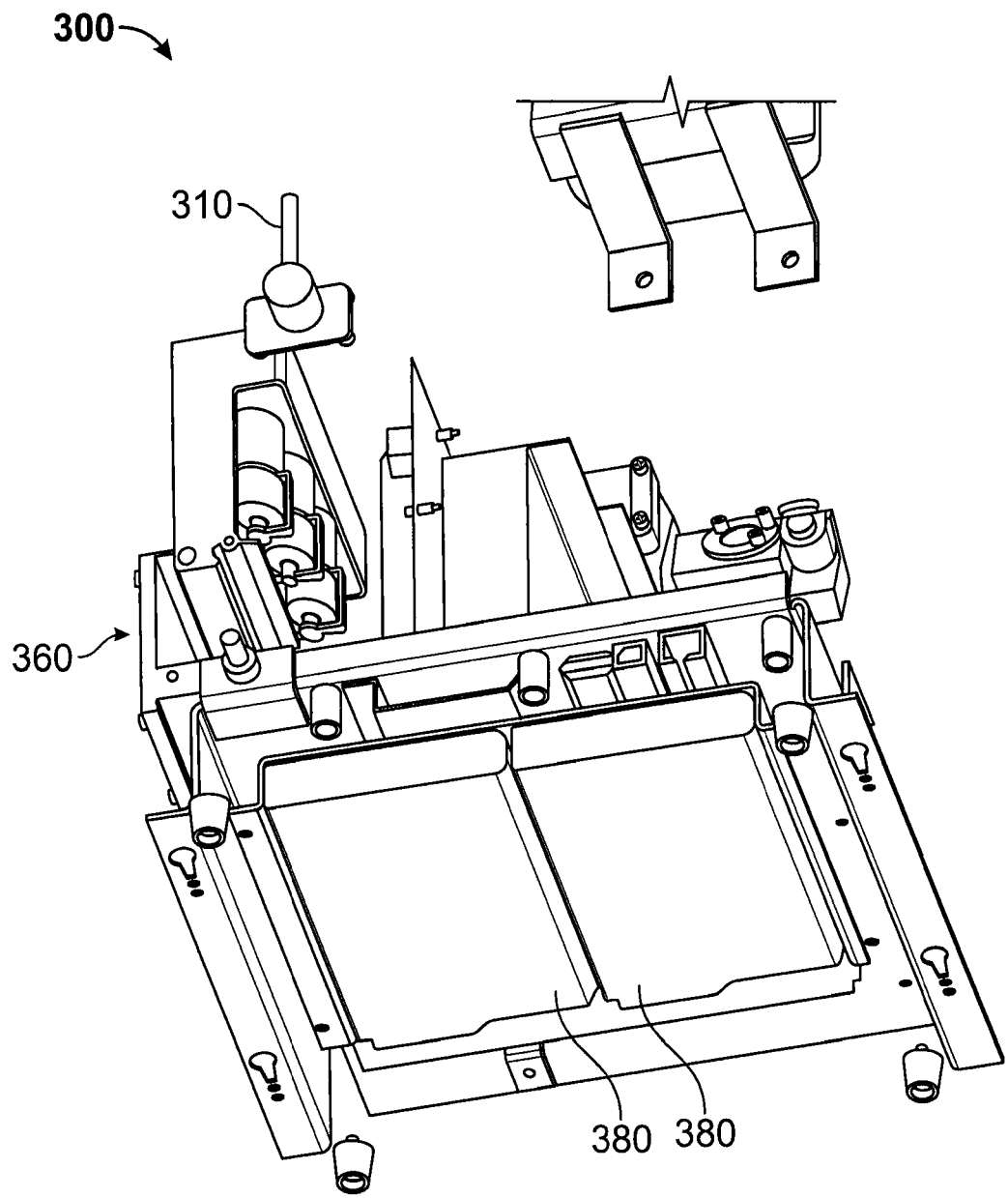
FIG. 6 is a bottom view of a partially exposed particle sizing system according to the invention.

Referring now to FIG. 4, in this example embodiment system 300 (with housing cover 301 off and shown from the rear of the unit) is comprised of a support chassis 303, a backpanel 306 attached to chassis 303 that includes at least 2 tubes protruding therefrom, an exhaust 360A and a charge sheath inlet 360B, along with an alcohol fill inlet 360C, a series of communication ports 360D and a power unit 380. In this example embodiment, power unit 380 is comprised of a pair of hot-swappable, rechargeable batteries 380 is also shown beneath chassis 303. In other embodiments, system 300 is powered by AC power and includes the option of switching from one power source to another. System optionally includes a charging unit for the rechargeable batteries that is powered from AC line power. The inlet to cyclone 310 is illustrated protruding from backpanel 306. Referring now to FIGS. 5 and 6 (with upper case 301 removed and display panel or screen 302 still in place) are other views of system 300 with the cover removed. Batteries 380 are included underneath system 300 on chassis 303 while cyclone 310 is also shown.

Figure 7A:
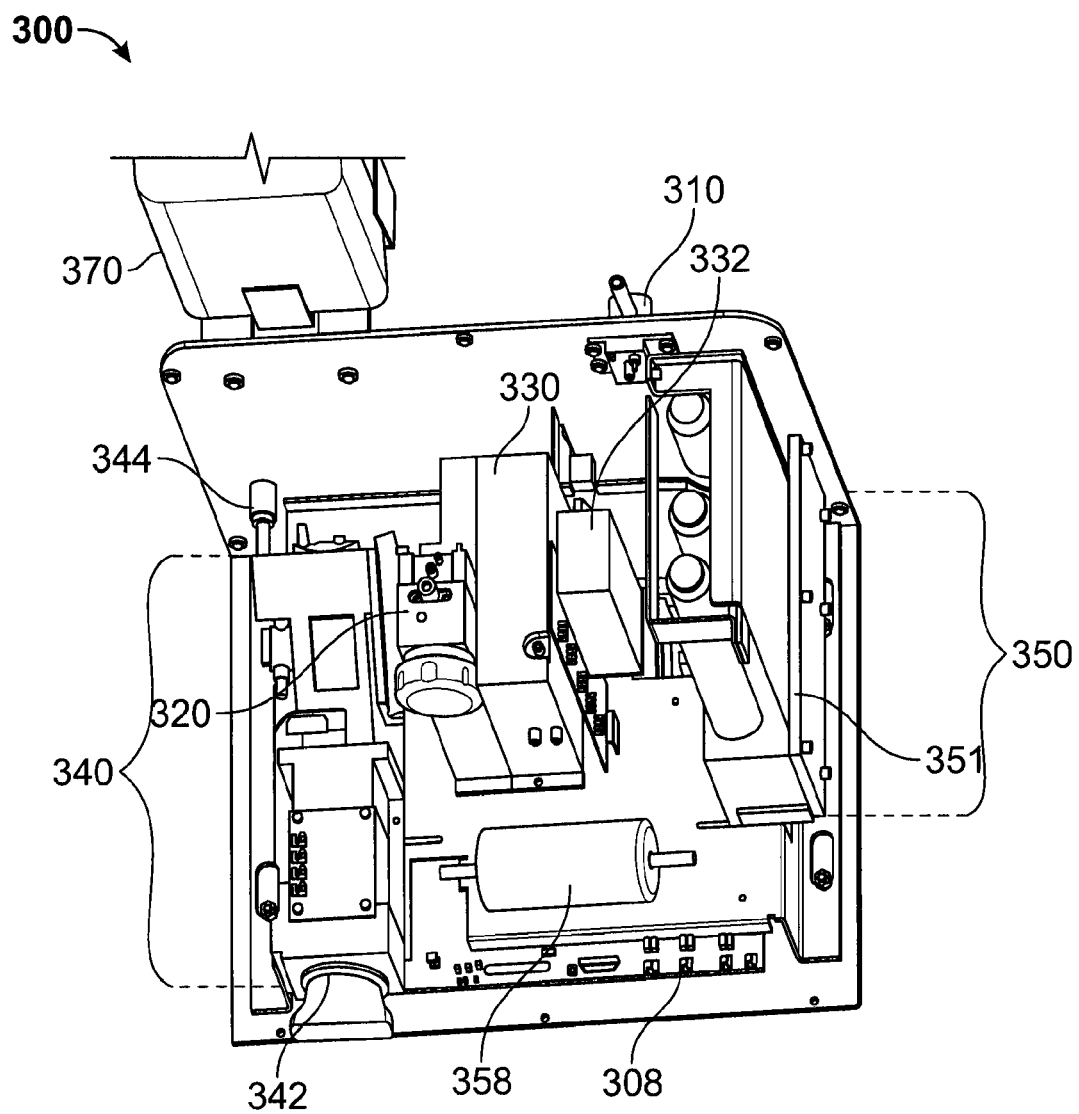
FIGS. 7A-7C are internal views of the nanoparticle sizing system according to the invention.
Figure 7B:
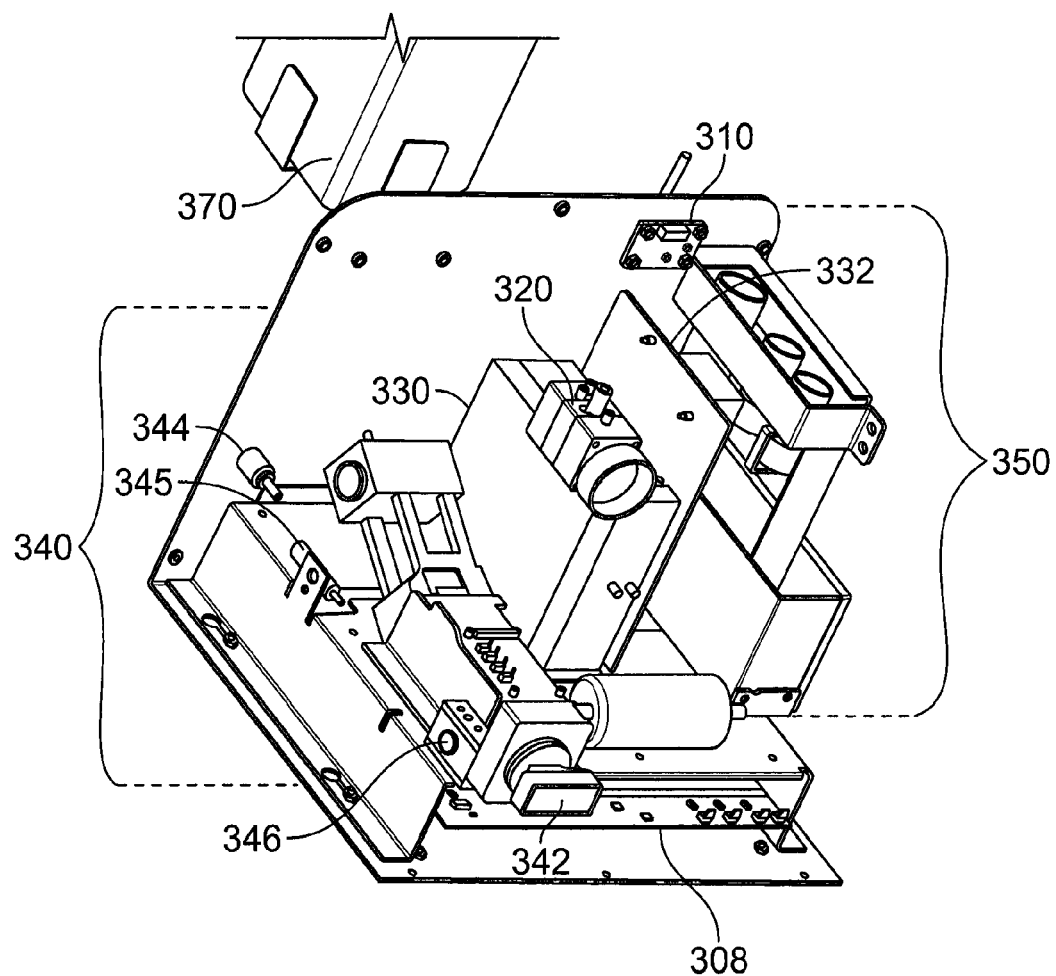
Figure 7C:
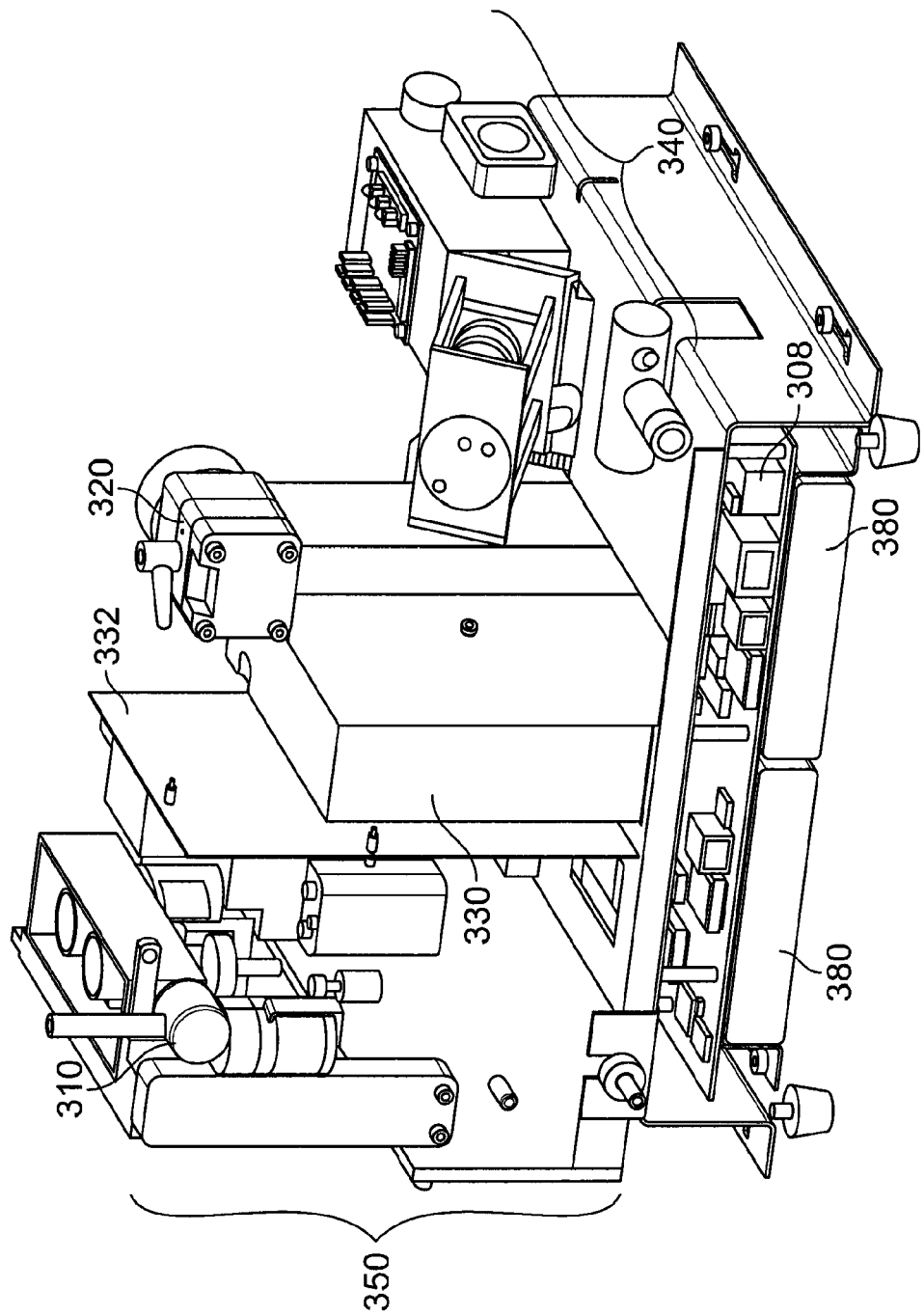

Referring now to FIGS. 7A-7C, in this example embodiment, there is illustrated internal views of nanoparticle sizing system 300 according to the invention. In this example embodiment, system 300 includes a main PC board 308, on top of chassis 303, which supports the majority of the system components and facilitates interconnectivity therebetween. Cyclone 310 protrudes from backpanel 306 and is adapted to be coupled to an ion charger 320 which in turn is coupled to a radial differential mobility analyzer (RDMA) 330. RDMA 330 has a high voltage PC board 332 connected thereto for charging the electrodes in RDMA 330. RDMA 330 is coupled to CPC assembly 340 which includes a removable wick assembly 342, an alcohol supply inlet 344, an alcohol reservoir fill valve 345 and an alcohol reservoir 346. CPC assembly 340 uses condensation particle counting technology as described in U.S. Pat. No. 4,790,650 to Keady and U.S. Pat. No. 5,118,959 to Caldow et al and an optical detection system as described in U.S. Pat. No. 6,831,279 to Ho et al, all of which are incorporated by reference in their entireties. RDMA 330 is generally connected to filters and other hardware to treat, control, and measure fluid flows. An extra working fluid fill bottle 370 is also included with system 300. In various example embodiments described herein, the particle counter device is selected from the group consisting of a condensation particle counter, an ultrafine condensation particle counter, an electrometer, an optical particle counter, a light-scattering particle counter, and a scanning mobility particle sizer.

A pump and manifold assembly 350 is also included in system 300 (see FIGS. 7A-7C) that substantially reduces the number of tubes that normally traverse a particle sizing system to enable sampled air to be channeled to the correct portion of system 300 for sizing and other air to be exhausted out of the system. In this example embodiment, manifold 350 includes a removable cover 351 to facilitate the changing of air filters and servicing of the manifold. In this example embodiment, system 300 includes circuitry for controlling the various desired measurements; for enabling stepped or scanned measurements (thereby generating a size distribution) or enabling fixed measurements (thereby generating a concentration measurement at a single size) and for operating the overall function of the scanning device.

Figure 8A:
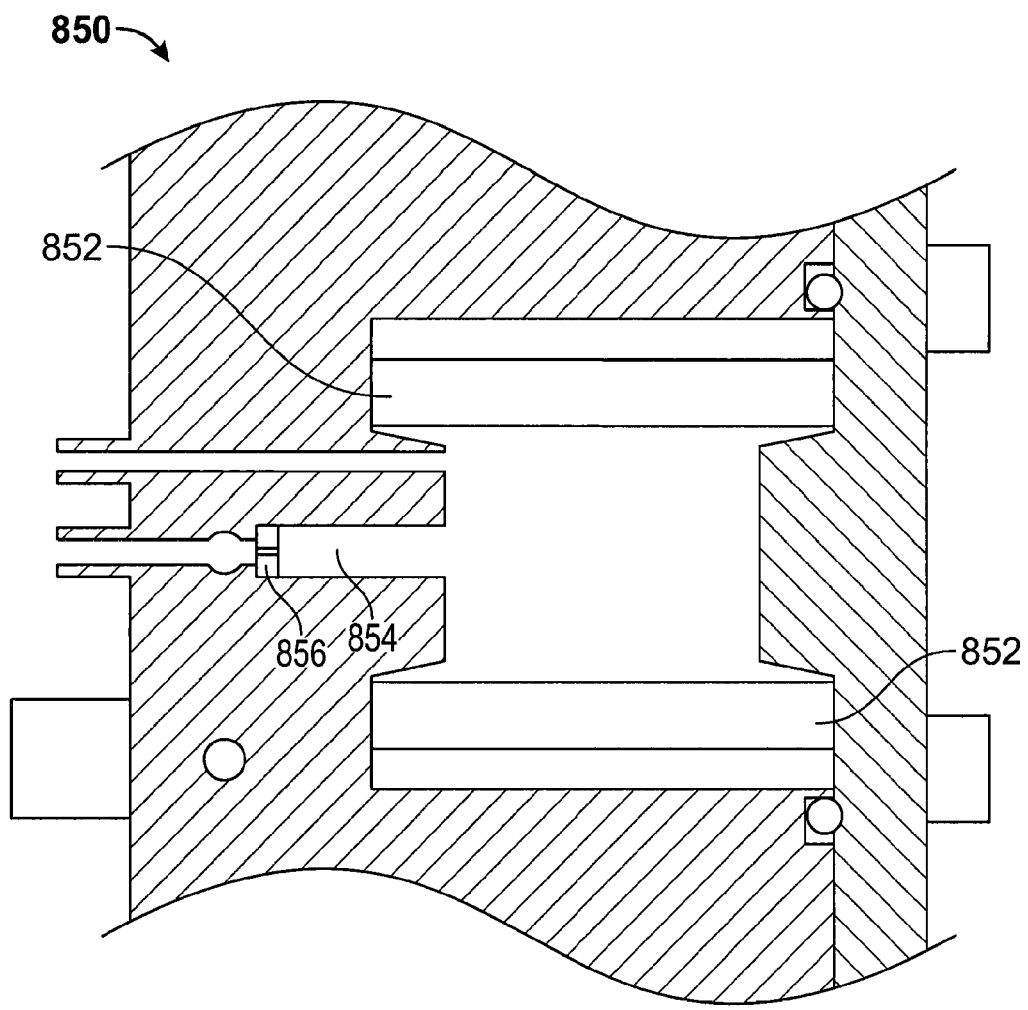
FIGS. 8A-8B are cutaway views of two embodiments of air filtering manifolds according to the invention.
Figure 8B:
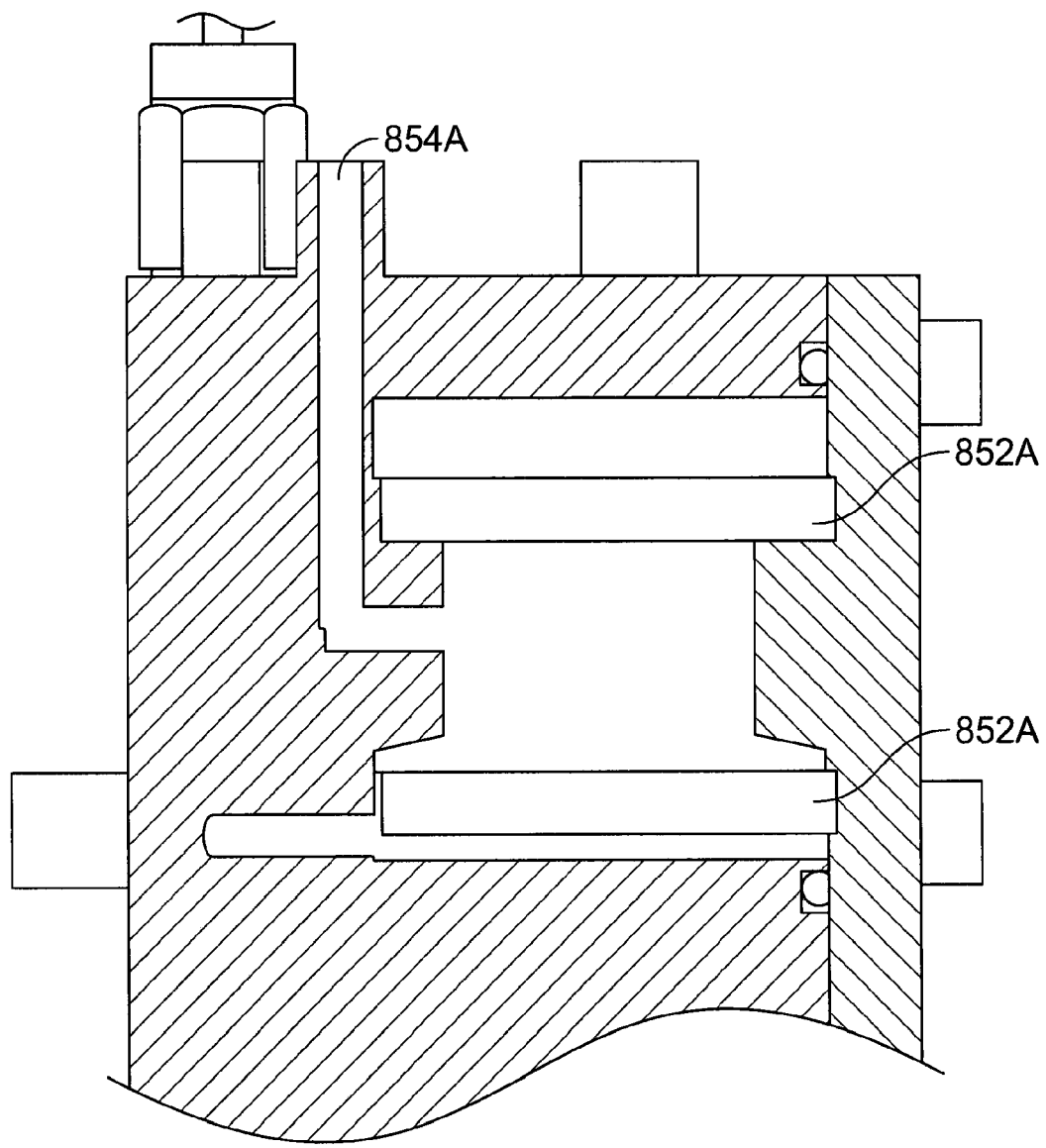

Referring now to FIGS. 8A-8B, there is shown example embodiments of improved filter and flow measurement manifold blocks 850 and 850A that help to form a manifold assembly 850 (FIG. 9A), which is an improvement over manifold 350 discussed above. These manifold block embodiments integrate filters, orifices and pressure ports into one manifold unit (as described herein in further detail) that is configurable to accommodate several flows and pumps depending upon the system configuration. FIGS. 8A-8B illustrate, in more detail, cutaway views of manifold block arrangements 850 and 850A which include filter media 852, flow restriction/measurement orifice 854, pressure taps for flow measurement 856 and various interconnections. The manifolds and individual manifold blocks also contain structures therein that allow for serviceability, manufacturability, and miniaturization via co-location of flow/filtration functions and minimizing the external interconnects for use in particle instruments and similar applications that require controlled and filtered gas flows. Manifold blocks 850 and 850A also include a means for combining repeatable units with external connections, with manifold mounted valves for controlling/restricting flow in a variable manner, and with branches of similar repeating units.

In general, flow systems are created to be driven by pumps, vacuum sources or pressure sources. Supply (positive flow) flows are distributed to external hardware, and are typically filtered and simultaneously measured. The flow measurement should be unobtrusive (i.e. does not affect flow being measured) and when made by measuring pressure drop across an orifice, should not be measured across the filter, as the pressure drop across a filter changes as the filter loads become clogged. This typically requires that the orifice be located away from the filter and generally requires additional tubing and fittings that are external to the filter. In the manifold blocks of the invention (effectively the repeatable block/units referred to above) the filter, orifice, and pressure taps are located near one another, generally along a single axis, with access to the filter media from one convenient direction. The geometry and structure of these units is such that interconnections between units can be made from many directions. For both the inlet and outlets to the filter, connections can be made from any path not parallel to the central axis. In the case of the outlet, small diameter connections (smaller than the central diameter of the filter media, not intersecting pressure taps) can be arranged along this path (see FIG. 8A).

Similar to this repeatable unit, return flows from an external device are also filtered. These units can also be combined or integrated into the manifold unit 850 thereby omitting the central orifice and pressure tap. The outlet of such a filter would be connected to a negative pressure source (e.g. the inlet to a pump for its protection). This repeatable manifold unit 850A is shown in FIG. 8B. The novel manifold designs have integrated pressure ports that are coaxial with orifice and filter, allowing for easy assembly and servicing. The arrangement allows for a single access panel and also for modularity that can be assembled for many applications, plus routing of inlet and outlet ports, control valves, etc., that are not features of other prior art manifolds.

Referring now to FIGS. 9A-9D, there are illustrated various views of air filtering manifold 850 according to the invention. In this example embodiment, manifold 850 is comprised of one or more repeatable manifold blocks therein and includes a removable cover 866, a charge sheath inlet tube 862 and an exhaust outlet tube protruding from one side. Various inlet and outlet ports are located on the top, side and a side opposite cover 866.

Figure 9A:
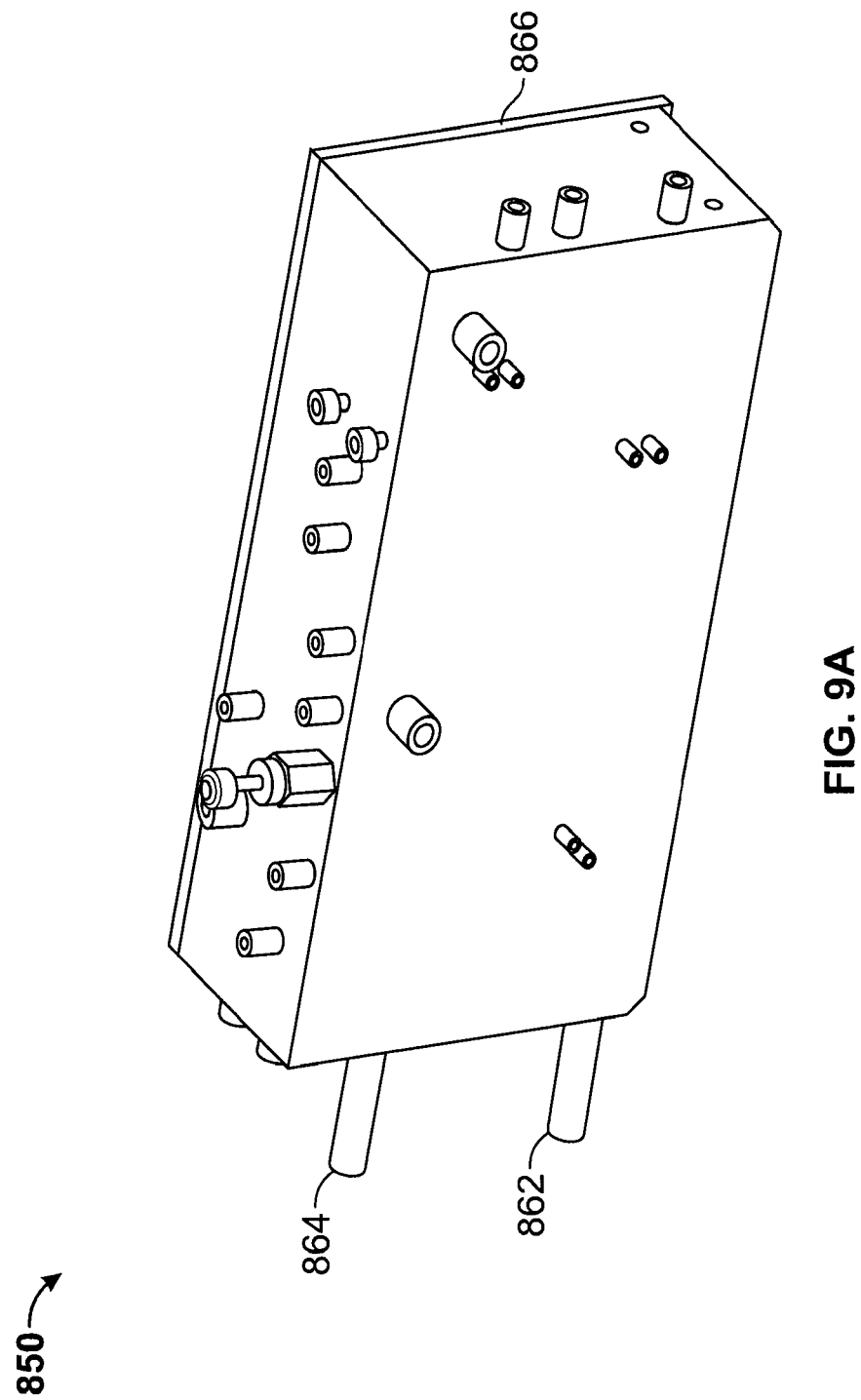
FIGS. 9A-9D are various views of the air filtering manifold according to the invention.
Figure 9B:
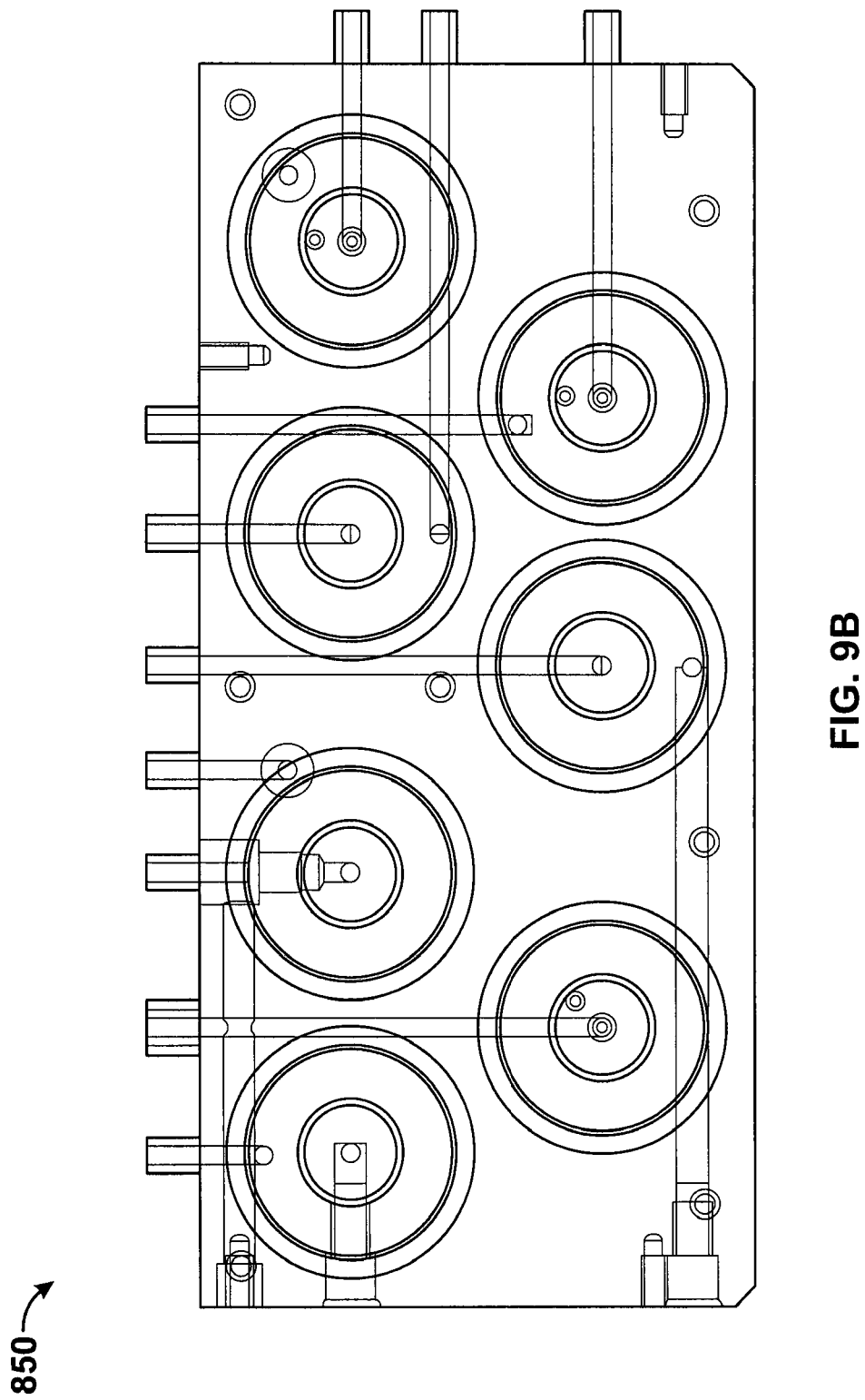

A typical flow system will also contain multiple branches, for instance where one pump supplies filtered air through two or more different filters or where two or more flows are filtered before exiting the system through a pump (the system exhaust). Such an arrangement is shown in FIG. 9B. These branches may also contain additional flow controls, such as valves, that can be implemented in this invention.

Figure 9C:
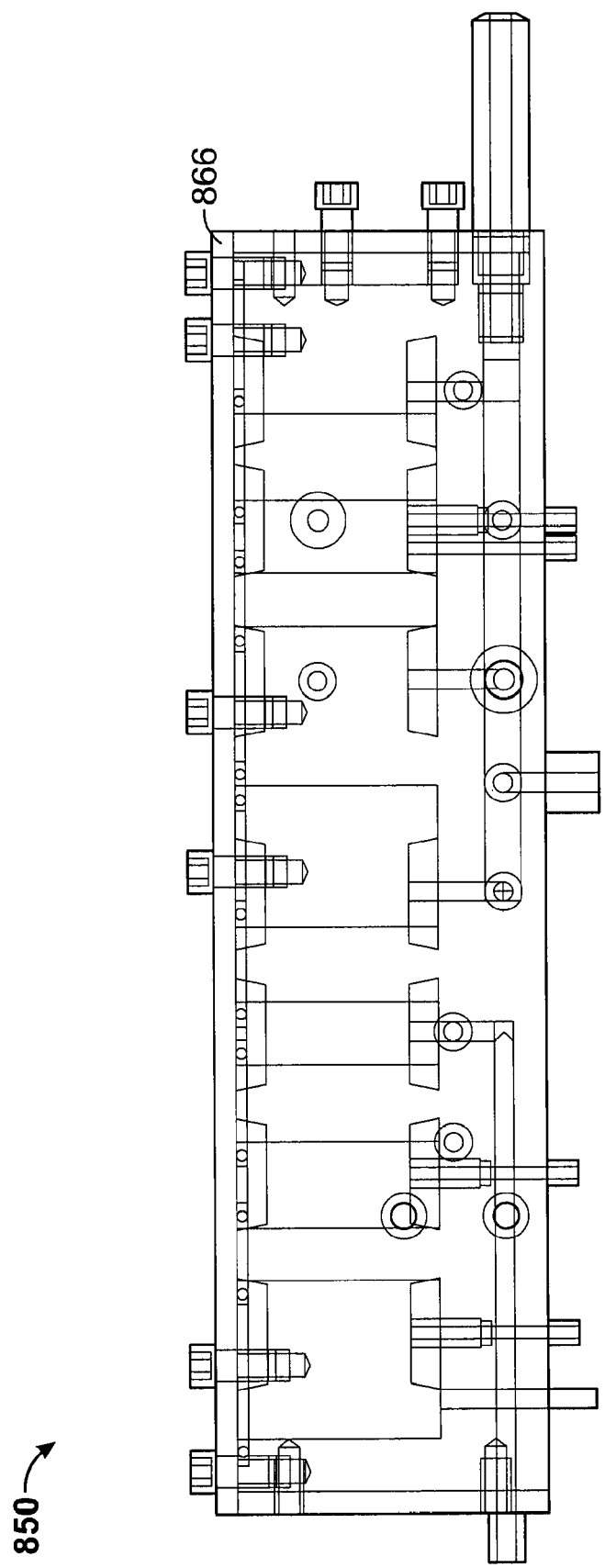
Figure 9D:
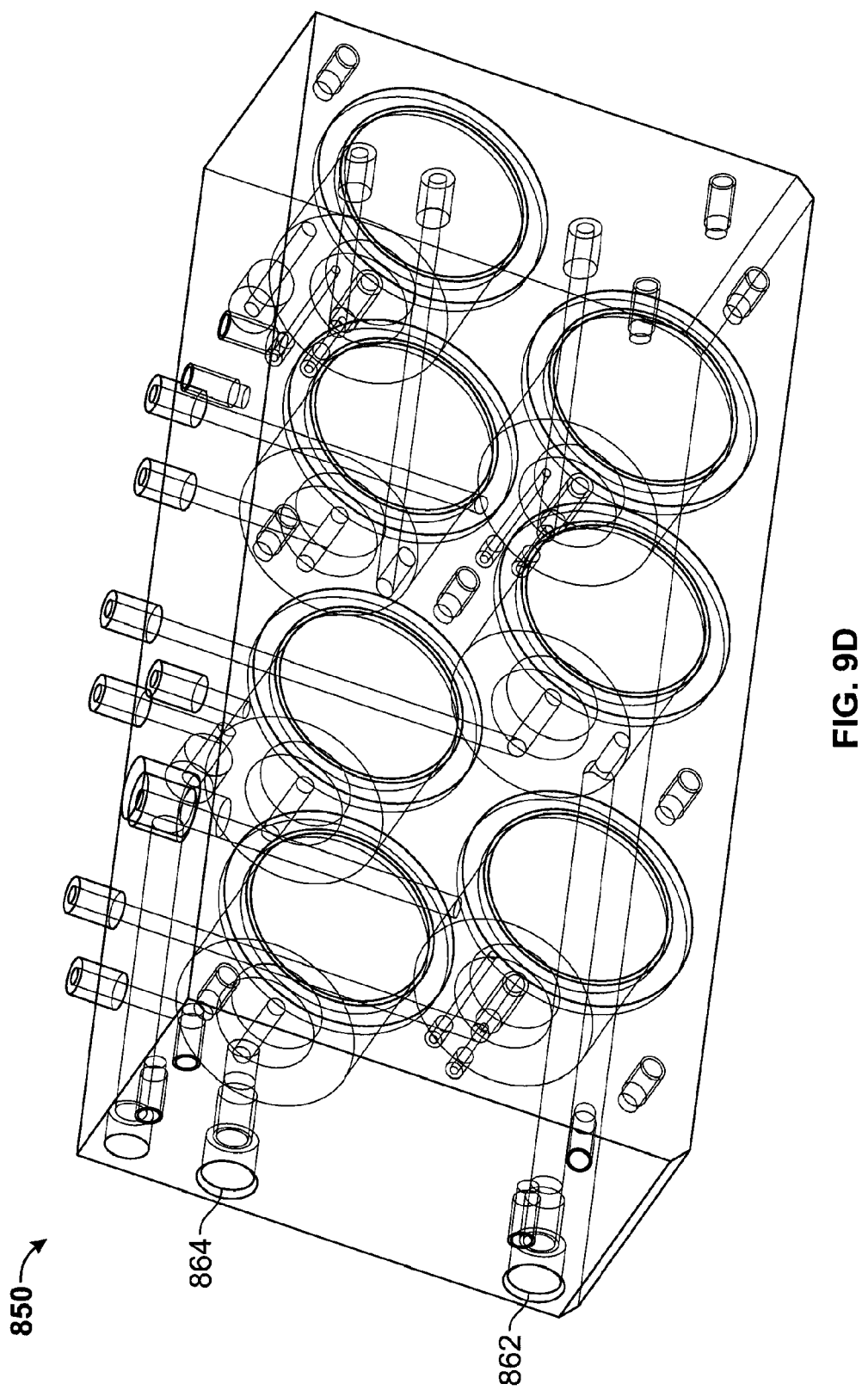

For a large flow system, these repeating filtering blocks/units and features may be combined into a single manifold with mostly repeating units. The complexity of interconnects and the size of externally connected components is all that controls the size of the resulting manifold, above and beyond the size of the repeating units. Manifold 850 shown in FIG. 9A is an example of reducing a flow system to a manifold of these repeating units is shown below. FIGS. 9B-9D illustrate side, top and perspective views of the internal structure of manifold assembly 850.

The design of the present manifold assembly solves the problem of serviceability and manufacturability of most filter manifolds by allowing assembly and replacement of filters from a single direction through a single unobstructed access panel, such as cover 866. The method of arranging filter units allows for ease of assembly of external tubing and vacuum/pressure sources and allow the designer to route connection so as to minimize tube length. The modularity and the design of the modular units allows for co-location of functions (filtration, flow measurement, and flow restriction/control), simplifying the construction of an aerosol instrument system. The filter units are small and internal connections allow for miniaturization, especially when compared to non-integrated solutions. Moreover, since it is a modular design as much as a fixed design, the basic units can be customized and combined for use in many different aerosol instrument applications.

In a related embodiment, the manifold system is configurable to join neighboring filters, to internally connect them to external pressure or vacuum sources, to connect filter cavities to additional external filters or flow treatment devices, or to incorporate valves or other devices to restrict, set, or control the various flows.

In other various embodiments, the nanoparticle scanning system and apparatus described herein include a novel manifold device having an orifice and pressure taps for measuring pressure drop are included in the same filter cavity unit, that the units are arranged such that interconnections are internal to a manifold, and that the units are designed to be modular so that they can be arranged for most aerosol flow applications. The invention is also unique in that all filter media can be installed from a single direction (for serviceability), can be changed depending on the desired level of filtration (more or less efficient), and that inlets and outlets to external devices (sources or sinks for the flow) can be arranged to minimize the length of tubing needed for these external interconnections.

As maintaining proper flows is critical to accurate measurements, such devices use one or various devices for measuring flows, such as thermal mass flow meters, or as in our current prototype, the pressure drop across a known geometry (a fixed orifice). Other methods may be used as well including the use of pressure drop for flow measurement which is especially useful because it is small in size and of limited power consumption.

In various embodiments of the inventions, there are included various (controlled or limited) pumps (internal or replaced by a means of connecting to external sources for moving gas flows), filters, tubes and other flow passages. These items may or may not be combined into manifolds, to reduce size and improve serviceability and manufacturability. For portability, any of the pumps should be internal, small, and of low power consumption. Such pumps require low flow size devices (like the RDMA) and low flow detectors (like a CPC), as large flows would require pumps with much larger power requirements (limiting or eliminating portability).

Various embodiments include circuitry for user interface, feedback, and reporting of measurements, as well as circuitry necessary for controlling flows, applying constant or time-varying voltages to the RDMA, for interpreting measurements/signals received from the CPC, and for other tasks. Finally, batteries are used for true portability. Such batteries may be internal, or removable. If removable, it would be ideal that they were also hot-swappable, as they are in this device. When used in a stationary mode, the device should also be usable with an external DC or AC power source.

The following U.S. patents and publications are herein incorporated by reference in their entirety: U.S. Pat. Nos. 5,117,190; 5,118,959; 5,596,136; 5,606,112; 5,620,100; 6,003,389; 6,012,343; 6,230,572; 6,568,245; 7,230,431 and 2011/0056273.

While the invention has been described in connection with certain preferred embodiments, there is no intent to limit it to those embodiments. On the contrary, it is recognized that various changes and modifications to the exemplary embodiments described herein will be apparent to those skilled in the art, and that such changes and modifications may be made without departing from the spirit and scope of the present invention. Therefore, the intent is to cover all alternatives, modifications and equivalents included within the spirit and scope of the invention as defined by the appended claims.

What is claimed is:

1. A particle sizing instrument, comprising:
   an electrical charging device adapted to bring ions into contact with a particle laden aerosol stream to effect a charging of the aerosol stream to produce electrically charged particles;
   a differential mobility analyzer operatively coupled to said electrical charging device and adapted to electrostatically remove excess ions and to selectively remove high electrical mobility particles from the aerosol stream;
   a condensation particle counter operatively coupled to said differential mobility analyzer and adapted to measure a number of particles in the aerosol stream; and
   a manifold assembly operatively coupled to the charging device and adapted to serve as a conduit for a sheath air flow to said electrical charging device and to provide an exhaust conduit for the particle laden aerosol stream exiting said condensation particle counter.

2. The instrument of claim 1 wherein the manifold assembly is further adapted to circulate at least two flows, a sheath flow that circulates as one loop in the instrument and through the differential mobility analyzer and another flow that circulates through the particle counter.

3. The instrument of claim 1 wherein the differential mobility analyzer is selected from the group consisting of a radial differential mobility analyzer, a cylindrical differential mobility analyzer, parallel plate differential mobility analyzer and a precipitator of various geometries.

4. The instrument of claim 1 further comprising a particle separator device adapted to separate particles of a predefined size from the particle laden aerosol stream.

5. The instrument of claim 4 wherein the particle separator device is selected from the group consisting of a cyclone, an impactor, and a virtual impactor.

6. The instrument of claim 1 wherein the electrical charging device is adapted to effect a diffusion charging of the aerosol stream.

7. The instrument of claim 1 wherein the charging device comprises an electrically conductive member adapted to provide a corona discharge.

8. The instrument of claim 1 further comprising a power source that facilitates portability of said instrument selected from the group consisting of at least one single use battery, a solar cell unit, a fuel cell, and a rechargeable battery unit.

9. The instrument of claim 1, wherein the electrical charging device is selected from the group consisting of a unipolar charger, a corona tip and metal mesh or screen arrangement, a diffusion charger, a photoionization charger, an ultraviolet light charger and an X-ray aerosol charger.

10. The instrument of claim 1, wherein the manifold assembly is comprised of at least one repeating block member adapted to direct air flow from a manifold inlet to a manifold outlet, the block member configured to be coupled to a second block member for directing a second air flow through the manifold assembly.

11. A particle sizing instrument comprising:
   an electrical charging device adapted to bring ions into contact with a particle laden aerosol stream to effect charging of the aerosol stream to produce electrically charged particles;
   a radial differential mobility analyzer operatively coupled to said electrical charging device and adapted to electrostatically remove excess ions and to selectively remove particles outside a predefined range of electrical mobilities from the aerosol stream;
   a particle counter device operatively coupled to said radial differential mobility analyzer and adapted to measure a number of particles in the aerosol stream;
   a manifold assembly operatively coupled to the particle charging device and adapted to serve as a conduit for a sheath air flow to said electrical charging device and to provide an exhaust conduit for the particle laden aerosol stream exiting said particle counter device; and
   a power source that facilitates portability of the instrument selected from the group consisting of at least one single use battery, a solar cell unit, a fuel cell, and a rechargeable battery unit.

12. The instrument of claim 11 wherein the manifold assembly is further adapted to circulate at least two flows, a sheath flow that circulates as one loop in the instrument and through the radial differential mobility analyzer and another flow that circulates through the particle counter device.

13. The instrument of claim 11 wherein the particle counter device is selected from the group consisting of a condensation particle counter, an ultrafine condensation particle counter, an electrometer, an optical particle counter, a light-scattering particle counter, and a scanning mobility particle sizer.

14. The instrument of claim 11 further comprising a particle separator device adapted to separate particles of a predefined size from the particle laden aerosol stream.

15. The instrument of claim 14 wherein the particle separator device is selected from the group consisting of a cyclone, an impactor, and a virtual impactor.

16. The instrument of claim 11 wherein the electrical charging device is adapted to effect a diffusion charging of the aerosol stream.

17. The instrument of claim 11 wherein the manifold assembly is comprised of at least one repeating block member adapted to direct air flow from a manifold inlet to a manifold outlet, the block member configured to be coupled to a second block member for directing a second air flow through the manifold assembly.

* * * * *